(12) United States Patent
Babbush et al.

(10) Patent No.: US 12,249,404 B2
(45) Date of Patent: Mar. 11, 2025

(54) EFFICIENT AND NOISE RESILIENT MEASUREMENTS FOR QUANTUM CHEMISTRY

(71) Applicant: Google LLC, Mountain View, CA (US)

(72) Inventors: Ryan Babbush, Venice, CA (US); William Huggins, Oakland, CA (US); Jarrod Ryan McClean, Marina del Rey, CA (US)

(73) Assignee: Google LLC, Mountain View, CA (US)

( * ) Notice: Subject to any disclaimer, the term of this patent is extended or adjusted under 35 U.S.C. 154(b) by 511 days.

(21) Appl. No.: 17/630,482

(22) PCT Filed: Jul. 28, 2020

(86) PCT No.: PCT/US2020/043884
§ 371 (c)(1),
(2) Date: Jan. 26, 2022

(87) PCT Pub. No.: WO2021/021813
PCT Pub. Date: Feb. 4, 2021

(65) Prior Publication Data
US 2022/0254453 A1 Aug. 11, 2022

Related U.S. Application Data

(60) Provisional application No. 62/879,750, filed on Jul. 29, 2019.

(51) Int. Cl.
*G16C 10/00* (2019.01)
*G06N 5/01* (2023.01)
(Continued)

(52) U.S. Cl.
CPC .............. *G16C 10/00* (2019.02); *G06N 5/01* (2023.01); *G06N 10/00* (2019.01); *G06N 10/60* (2022.01)

(58) Field of Classification Search
USPC .......................................................... 702/30
See application file for complete search history.

(56) References Cited

U.S. PATENT DOCUMENTS

| 2016/0283857 A1 | 9/2016 | Babbush et al. |
| 2018/0053112 A1 | 2/2018 | Bravyi et al. |

(Continued)

OTHER PUBLICATIONS

Aquilante et al., "MOLCAS 7: The Next Generation," Journal of computational chemistry, Jan. 15, 2010, 31(1):224-247.

(Continued)

*Primary Examiner* — Paul D Lee
(74) *Attorney, Agent, or Firm* — Fish & Richardson P.C.

(57) ABSTRACT

Methods, systems and apparatus for measuring the energy of a quantum chemical system. In one aspect, a method includes obtaining a Hamiltonian describing the chemical system, where the Hamiltonian is expressed in an orthonormal basis; decomposing the Hamiltonian into a sum of terms where each term comprises a respective operator that effects a respective single particle basis rotation, and one or more particle density operators; repeatedly, for each group comprising terms with a same operator that effects a respective single particle basis rotation, measuring expectation values of the terms included in the group, comprising: performing the respective single particle basis rotation on a qubit system encoding a state of the chemical system; and measuring Jordan-Wigner transformations of the one or more particle density operators in the group to obtain a respective measurement result for the group; and determining the energy of the chemical system using the obtained measurement results.

13 Claims, 7 Drawing Sheets

(51) Int. Cl.
G06N 10/00 (2022.01)
G06N 10/60 (2022.01)

(56) References Cited

U.S. PATENT DOCUMENTS

| | | | | |
|---|---|---|---|---|
| 2018/0341874 | A1 | 11/2018 | Puri et al. | |
| 2019/0318053 | A1* | 10/2019 | Low | G06F 30/20 |
| 2020/0184023 | A1* | 6/2020 | Delaney | G16C 10/00 |
| 2020/0226487 | A1* | 7/2020 | Radin | G06N 10/60 |
| 2020/0364601 | A1* | 11/2020 | Yamazaki | G06N 10/20 |
| 2021/0272009 | A1* | 9/2021 | Gidney | H03K 19/20 |

OTHER PUBLICATIONS

Beebe et al., "Simplifications in the generation and transformation of two-electron integrals in molecular calculations," International Journal of Quantum Chemistry, Oct. 1977, 12(4):683-705.
Berry et al., "Qubitization of arbitrary basis quantum chemistry by low rank factorization," arXiv, Feb. 6, 2019, 20 pages.
Bonet-Monroig et al., "Low-cost error mitigation by symmetry verification," Physical Review A, Dec. 28, 2018, 98(6):062339, 10 pages.
Bravyi et al., "Fermionic quantum computation," Annals of Physics, 2002, 298(1):210-226.
Clements et al., "Optimal design for universal multiport interferometers," Optica, Dec. 2016, 3(12):1460-1465.
International Preliminary Report on Patentability in International Appln. No. PCT/US2020/043884, dated Feb. 10, 2022, 8 pages.
International Search Report and Written Opinion in International Appln. No. PCT/US2020/043884, dated Nov. 4, 2020, 14 pages.
Izmaylov et al., "Revising the measurement process in the variational quantum eigensolver: is it possible to reduce the number of separately measured operators?" Chemical Science, Feb. 12, 2019, 10:3746-3755.
Jiang et al., "Majorana loop stabilizer codes for error correction of fermionic quantum simulations," arXiv, Dec. 19, 2018, 13 pages.
Kandala et al., "Hardware-efficient variational quantum eigensolver for small molecules and quantum magnets," Nature, Sep. 14, 2017, 549(7671):242-246.
Kivlichan et al., "Quantum Simulation of Electronic Structure with Linear Depth and Connectivity," Physical review letters, Mar. 13, 2018, 120(11):110501, 6 pages.
Koch et al., "Reduced scaling in electronic structure calculations using Cholesky decompositions," The Journal of chemical physics, May 14, 2003, 118(21):9481-9484.
Lee et al., "Generalized Unitary Coupled Cluster Wave functions for Quantum Computation," Journal of Chemical Theory and Computation, Nov. 28, 2018, 15(1):311-324.
Mardirossian et al., "Lowering of the complexity of quantum chemistry methods by choice of representation," The Journal of chemical physics, Jan. 23, 2018, 148(4):044106.
McArdle et al., "Error mitigated quantum computational chemistry," arXiv, Jul. 6, 2018, 11 pages.
McArdle et al., "Error-Mitigated Digital Quantum Simulation," Physical Review Letters, May 8, 2019, 122(18):180501, 6 pages.
McClean et al., "Decoding quantum errors with subspace expansions," arXiv, Mar. 14, 2019, 12 pages.
McClean et al., "Hybrid quantum-classical hierarchy for mitigation of decoherence and determination of excited states," Physical Review A, Apr. 6, 2017, 95(4):042308, 10 pages.
McClean et al., "The theory of variational hybrid quantum-classical algorithms," New Journal of Physics, Feb. 5, 2016, 18(2):023023, 23 pages.
Motta et al., "Low rank representations for quantum simulation of electronic structure," arXiv, Aug. 9, 2018, 8 pages.
O'Gorman et al., "Generalized swap networks for near-term quantum computing," arXiv, May 13, 2019, 16 pages.
O'Brien et al., "Calculating energy derivatives for quantum chemistry on a quantum computer," arXiv, Jul. 17, 2019, 21 pages.
O'Malley et al., Scalable Quantum Simulation of Molecular Energies. Physical Review X, Jul. 18, 2016, 6(3):31007, 13 pages.
Otten et al., "Accounting for errors in quantum algorithms via individual error reduction," npj Quantum Information, Jan. 29, 2019, 5(1):11, 6 pages.
Parrish et al., "Quantum Computation of Electronic Transitions Using a Variational Quantum Eigensolver," Physical Review Letters, Jun. 12, 2019, 122(23):230401, 6 pages.
Peruzzo et al., "A variational eigenvalue solver on a photonic quantum processor," Nature Communications, Jul. 23, 2014, 5:4213, 7 pages.
Purwanto et al., "Assessing weak hydrogen binding on Ca+ centers: An accurate many-body study with large basis sets," The Journal of chemical physics, Oct. 28, 2011, 135(16):164105, 12 pages.
Romero et al., "Strategies for quantum computing molecular energies using the unitary coupled cluster ansatz," arXiv, Jan. 10, 2017, 18 pages.
Rubin et al., "Application of fermionic marginal constraints to hybrid quantum algorithms," arXiv, May 15, 2018, 24 pages.
Rubin et al., "Application of fermionic marginal constraints to hybrid quantum algorithms," New Journal of Physics, May 9, 2018, 20(5):053020, 22 pages.
Sagastizabal et al., "Error Mitigation by Symmetry Verification on a Variational Quantum Eigensolver," arXiv, Feb. 28, 2019, 13 pages.
Santagati et al., "Witnessing eigenstates for quantum simulation of Hamiltonian spectra," arXiv, Jan. 15, 2018, 27 pages.
Setia et al., "Bravyi-Kitaev Superfast simulation of electronic structure on a quantum computer," The Journal of chemical physics, Apr. 25, 2018, 148(16):164104, 14 pages.
Temme et al., "Error Mitigation for Short-Depth Quantum Circuits," Physical review letters, Nov. 3, 2017, 119(18):180509, 5 pages.
Wecker et al., "Progress towards practical quantum variational algorithms," Physical Review A, Oct. 2, 2015, 92(4):042303, 10 pages.
Wecker et al., "Towards Practical Quantum Variational Algorithms," Sep. 8, 2015, 11 pages.
Notice of Allowance in Australian Appln. No. 2020323522, dated Jul. 26, 2023, 3 pages.
Office Action in Canadian Appln. No. 3146219, dated Feb. 22, 2023, 5 pages.
Notice of Allowance in Australian Appln. No. 2023248100, mailed on Jun. 20, 2024, 3 pages.
Office Action in Chinese Appln. No. 202080055624.7, mailed on Jun. 29, 2024, 13 pages (with English translation).

* cited by examiner

EFFICIENT AND NOISE RESILIENT MEASUREMENTS FOR QUANTUM CHEMISTRY

CROSS-REFERENCE TO RELATED APPLICATIONS

This application is a National Stage Application under 35 U.S.C. § 371 and claims the benefit of International Application No. PCT/US2020/043884, filed on Jul. 28, 2020, which claims priority to U.S. Patent Application Ser. No. 62/879,750, filed on Jul. 29, 2019. The disclosure of the prior application is considered part of and is incorporated by reference in the disclosure of this application.

BACKGROUND

This specification relates to quantum computing.

Quantum measurement is a central component of experimental quantum computations. Performing one measurement round requires preparing a quantum system in a particular state and applying quantum operations and measurements with high-precision control to the quantum system. Performing a measurement round is therefore costly.

SUMMARY

This specification describes measurement strategies for quantum chemistry.

In general, one innovative aspect of the subject matter described in this specification can be implemented in a method for measuring the energy of a chemical system, the method comprising: obtaining a Hamiltonian describing the chemical system, wherein the Hamiltonian is expressed in an orthonormal basis; decomposing, by classical computation, the Hamiltonian describing the chemical system into a sum of terms wherein each term comprises i) a respective operator that effects a respective single particle basis rotation, and ii) one or more particle density operators; repeatedly, for each group comprising terms with a same operator that effects a respective single particle basis rotation, measuring expectation values of the terms included in the group, comprising: performing, by quantum computation, the respective single particle basis rotation on a qubit system encoding a state of the chemical system; and measuring, in the computational basis, Jordan-Wigner transformations of the one or more particle density operators in the group to obtain a respective measurement result for the group; and determining, by classical computation, the energy of the chemical system using the obtained measurement results.

Other implementations of this aspect include corresponding computer systems, apparatus, and computer programs recorded on one or more computer storage devices, each configured to perform the actions of the methods. A system of one or more classical and quantum computers can be configured to perform particular operations or actions by virtue of having software, firmware, hardware, or a combination thereof installed on the system that in operation causes or cause the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination. In some implementations measuring expectation values of the terms included in the group further comprises performing error mitigation by post selection. Performing error mitigation by post selection can include: computing a total particle number or spin component using the obtained measurement result; determining whether the computed total particle number or spin component is equal to a respective target value; in response to determining that the computed total particle number or spin component is equal to a respective target value, providing the measurement result for determining, by classical computation, the energy of the chemical system; and in response to determining that the computed total particle number or spin component is not equal to a respective target value, discarding the measurement result.

In some implementations the Hamiltonian describing the chemical system comprises a one-electron component and a two-electron component, and wherein decomposing, by classical computation, the Hamiltonian describing the chemical system into a sum of terms comprises: diagonalizing each scalar coefficient in the two-electron component, comprising representing each scalar coefficient in the two-electron component as a second sum of terms over the single particle bases, each term in the second sum of terms comprising a product of a Hermitian coefficient matrix of one-body operators formed by a first pair of spin orbitals, a matrix, and a Hermitian coefficient matrix of one-body operators formed by a second pair of spin orbitals; determining, for each term in the sum of terms, a matrix that diagonalizes the one-body operators in the respective Hermitian coefficient matrices; and determining the respective operators that effect the respective basis rotations using the determined matrices that diagonalize the one-body operators.

In some implementations the method further comprises discarding finite eigenvalues smaller than a predetermined threshold.

In some implementations the method further comprises grouping terms of the decomposed Hamiltonian that are diagonal in the same single particle basis, comprising, for each term in the decomposed Hamiltonian: determining which single particle basis the term diagonalizes; and assigning the term to a group corresponding to the determined single particle basis.

In some implementations measuring expectation values of the terms included in the group comprises measuring the expectation values of the terms included in the group simultaneously.

In some implementations performing the respective basis rotation comprises applying a respective Givens rotation circuit to the qubit system.

In some implementations determining, by classical computation, the energy of the chemical system using the obtained measurement results comprises: determining an average measurement result corresponding to each group; and adding the determined averages.

In some implementations the arbitrary orthonormal basis comprises a Gaussian or molecular orbital basis.

In some implementations the Hamiltonian describing the chemical system comprises multiple terms each comprising products of one or more of i) annihilation operators for respective spin orbitals, ii) creation operators for respective spin orbitals, and ii) scalar coefficients given by one- or two-electron integrals over basis functions in the orthonormal basis.

In some implementations the chemical system comprises a symmetrically stretched Hydrogen chain, symmetrically stretched water molecule, or a stretched Nitrogen dimer.

The subject matter described in this specification can be implemented in particular ways so as to realize one or more of the following advantages. The presently described disclosure represents a significant and widely applicable improvement to the state of the art in quantum measurement. The presently described measurement strategy reduces the time required to measure the energy of a quantum system, e.g., in quantum chemistry, to within a fixed accuracy. In addition, the presently described measurement strategy can be implemented to perform measurements that are less sensitive to readout errors compared to measurements performed using naïve strategies. Furthermore, the presently described measurement strategy enables a powerful form of error mitigation to be implemented at a minimal cost.

The details of one or more implementations of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

The variational quantum eigensolver (VQE) framework is an example of one promising path towards fruitfully utilizing small and noisy quantum devices for simulating quantum chemistry. The VQE approach uses a quantum device as a co-processor which prepares a parameterized quantum wavefunction and measures the expectation value of observables. In conjunction with a classical optimization algorithm it is possible to minimize the expectation value of the Hamiltonian as a function of the parameters, approximating the wavefunction, energy, and other properties of the ground state.

One difficulty associated with using VQE to target nontrivial systems is the large number of circuit repetitions needed to perform accurate measurements. In the VQE framework expectation values are computed by Hamiltonian averaging, where the Hamiltonian is decomposed into a sum of easily measured operators, e.g., Pauli strings, whose expectation values are sampled independently by repeated measurement. When measurements are distributed optimally between these easy-to-sample operators $H_l$, the total number of measurements M required is upper bounded by $M \leq (\Sigma_l |\omega_l|/\epsilon)^2$ where $H = \Sigma_l \omega_l H_l$ represents the Hamiltonian whose expectation value is estimated as $\Sigma_l \omega_l \langle H_l \rangle$, $\omega_l$ represent scalars and $\epsilon$ represents target precision. Techniques for assessing the viability of VQE typically apply this type of upper bound therefore conclude that chemistry applications require a significantly large number of measurements.

This specification describes an improved measurement strategy that is based on a decomposition of the two-electron integral tensor and does not rely on properties of easy-to-measure operators such as Pauli strings. The decomposition of the two-electron integral tensor results in fewer sets of terms to be measured separately and requires a smaller number of repetitions to measure the ground state for fixed accuracy. For example, the measurement strategy can provide a reduction in the required total number of measurements by up to four orders of magnitude. In addition, the measurement strategy is less sensitive to readout errors caused by long Jordan-Wigner strings compared to existing measurement strategies. Furthermore, the measurement strategy provides a powerful form of error mitigation at a minimal cost by allowing for post selection by simultaneously measuring the total particle number or spin operators with each measurement shot.

Example Hardware

Figure 1:
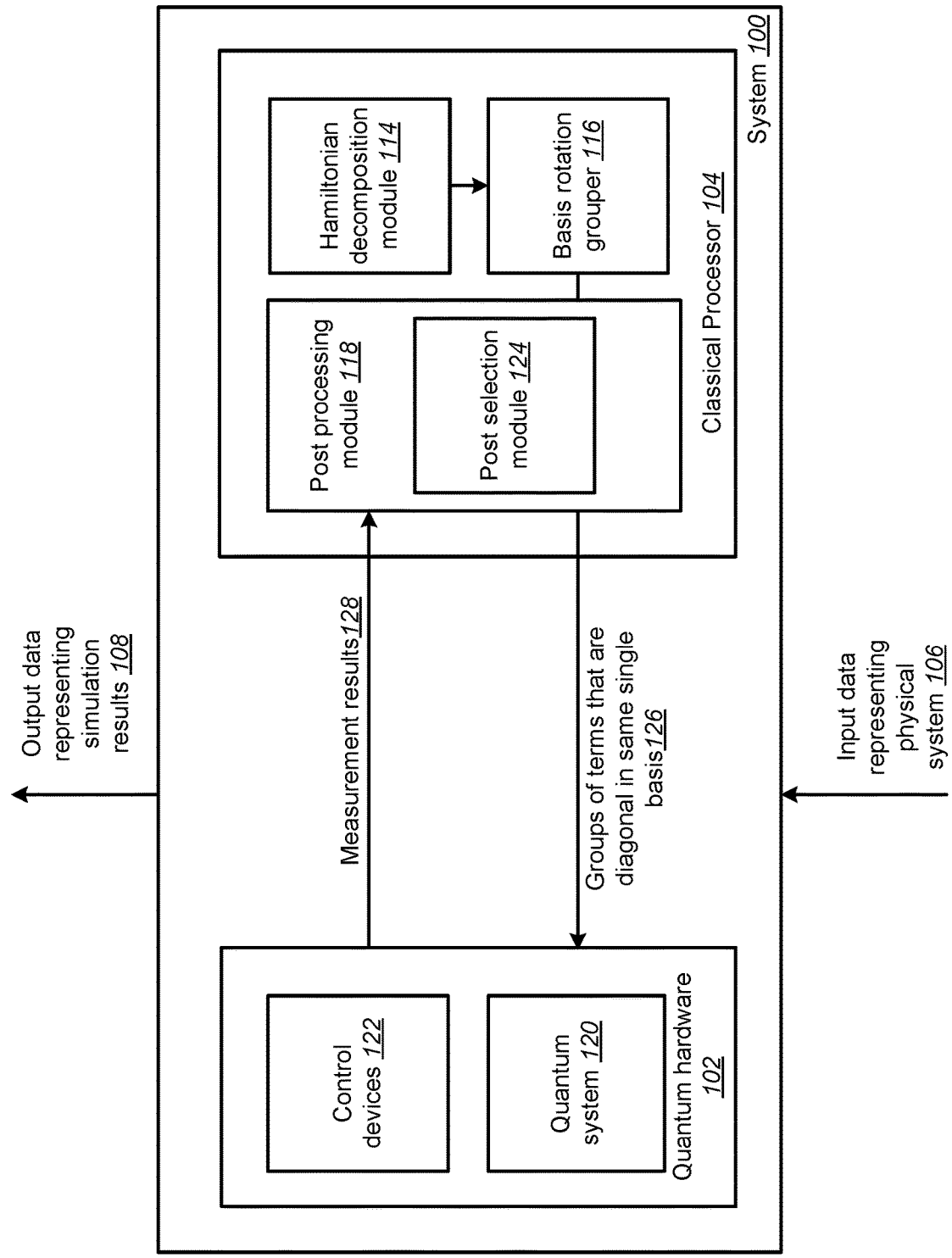
FIG. 1 depicts an example quantum computation system.

FIG. 1 depicts an example quantum computing system 100 suitable for implementing the presently described measurement strategy. The example system 100 is an example of a system implemented as classical or quantum computer programs on one or more classical computers or quantum computing devices in one or more locations, in which the systems, components, and techniques described below can be implemented.

The system 100 may include quantum hardware 102 in data communication with a classical processor 104. For convenience, the classical processor 104 and quantum hardware 102 are illustrated as separate entities, however in some implementations the classical processor 104 can be included in quantum hardware 102, e.g., the quantum hardware 102 can include one or more components for performing classical computing operations.

The system 100 may receive as input data that may include data representing a physical system of interest, e.g., input data 106. The received data representing a physical system of interest may include data representing a physical system that is to be probed or simulated. For example, the energy of the physical system may need to be determined. In some implementations the received data may represent a physical system that is described by an electronic structure Hamiltonian, e.g., a single atom or molecule, material, or a chemical.

The system may generate as output data representing results of simulating the physical system of interest, e.g., output data 108. The output data 108 may include data representing determined properties of the physical system, e.g., a measured energy of the physical system, or data that may be used to determine properties of the physical system, e.g., data representing raw measurement results. For example, as described above, in some implementations the physical system may be a chemical, e.g. an atom or molecule. In these cases data representing simulation results may be used to determine properties of the chemical, e.g., a rate of a chemical reaction, electronic structure, and/or optical/thermal properties.

The system 100 is configured to perform classical computations in combination with quantum computations using the classical processor 104 and quantum hardware 102. The quantum hardware 102 includes components for performing quantum computations using quantum circuits. For example, the quantum hardware 102 includes a quantum system 120 and control devices 122. The quantum system 120 includes one or more multi-level (e.g. two-level) quantum subsystems, e.g., qubits, that are used to perform algorithmic operations or quantum computations. The specific realization of the multi-level quantum subsystems that the quantum hardware 102 includes and how they interact with one another is dependent on a variety of factors including the type of quantum computations that the quantum hardware 102 is performing. For example, the multi-level quantum subsystems may include qubits that are realized via atomic, molecular or solid-state quantum systems. In other examples the qubits may include, but are not limited to, superconducting qubits or semi-conducting qubits.

The multi-level quantum subsystems can be frequency tunable. For example, each qubit may have associated operating frequencies that can be adjusted, e.g., using one or more control devices 122, through application of voltage pulses via one or more drivelines coupled to the qubit. Example operating frequencies include qubit idling frequencies, qubit interaction frequencies, and qubit readout frequencies. Different frequencies correspond to different operations that the qubit can perform. For example, setting the operating frequency to a corresponding idling frequency may put the qubit into a state where it does not strongly interact with other qubits, and where it may be used to perform single-qubit gates (e.g., as part of a quantum circuit). As another example, in cases where qubits interact via couplers with fixed coupling, qubits can be configured to interact with one another by setting their respective operating frequencies at some gate-dependent frequency detuning from their common interaction frequency. In other cases, e.g., when the qubits interact via tunable couplers, qubits can be configured to interact with one another by setting the parameters of their respective couplers to enable interactions between the qubits and then by setting the qubit's respective operating frequencies at some gate-dependent frequency detuning from their common interaction frequency. Such interactions may be performed in order to perform multi-qubit gates (e.g., as part of a quantum circuit).

The control devices 122 can further include measurement devices, e.g., readout resonators. Measurement results (measurement data) obtained via measurement devices may be provided to classical processors included in the quantum hardware 102 or to the classical processor 104 for processing and analyzing.

The classical processor 104 may include a Hamiltonian decomposition module 114 that is configured to process received input data, e.g., data representing a Hamiltonian expressed in an orthonormal basis such as a Gaussian or general molecular orbital basis, to generate data representing a decomposed version of the Hamiltonian that is equivalent to or approximates the Hamiltonian expressed in the orthonormal basis.

The decomposed version of the Hamiltonian includes a sum of terms where the sum of terms includes diagonal operators in respective single particle bases. For example, as described in more detail below with reference to FIG. 2, each term in the sum of terms can include i) a respective operator that effects a respective basis rotation, and ii) one or more particle density operators. An example process for decomposing a Hamiltonian describing a chemical system into such a sum of terms is described in detail below with reference to FIG. 2.

The classical processor 104 may also include a basis rotation grouper 116 that is configured to group terms of the decomposed Hamiltonian that are diagonal (composed of sums and products of particle density operators) in the same single particle basis. The basis rotation grouper 116 is configured to provide the quantum hardware 102 with data representing the groups of terms that are diagonal in the same single particle basis 126. The quantum hardware 102 can then measure the expectation values of the terms associated with each single particle basis by applying a Givens rotation circuit which performs a change of basis before measuring the Jordan-Wigner transformed number operators in the computational basis. An example process for grouping terms of a decomposed Hamiltonian and measuring expectation values of terms in a group is described in more detail below with reference to FIG. 2.

The classical processor 104 may also include a post processing module 118 that is configured to process measurement results 128 received from the quantum hardware 102. For example, the post processing module 118 can be configured to compute statistical averages of measurement results. In some implementations the post processing module 118 may also include a post selection module 124 for performing error mitigation, as described in more detail below with reference to FIG. 4.

Basis Rotation Grouping Measurement Strategy

Figure 2:
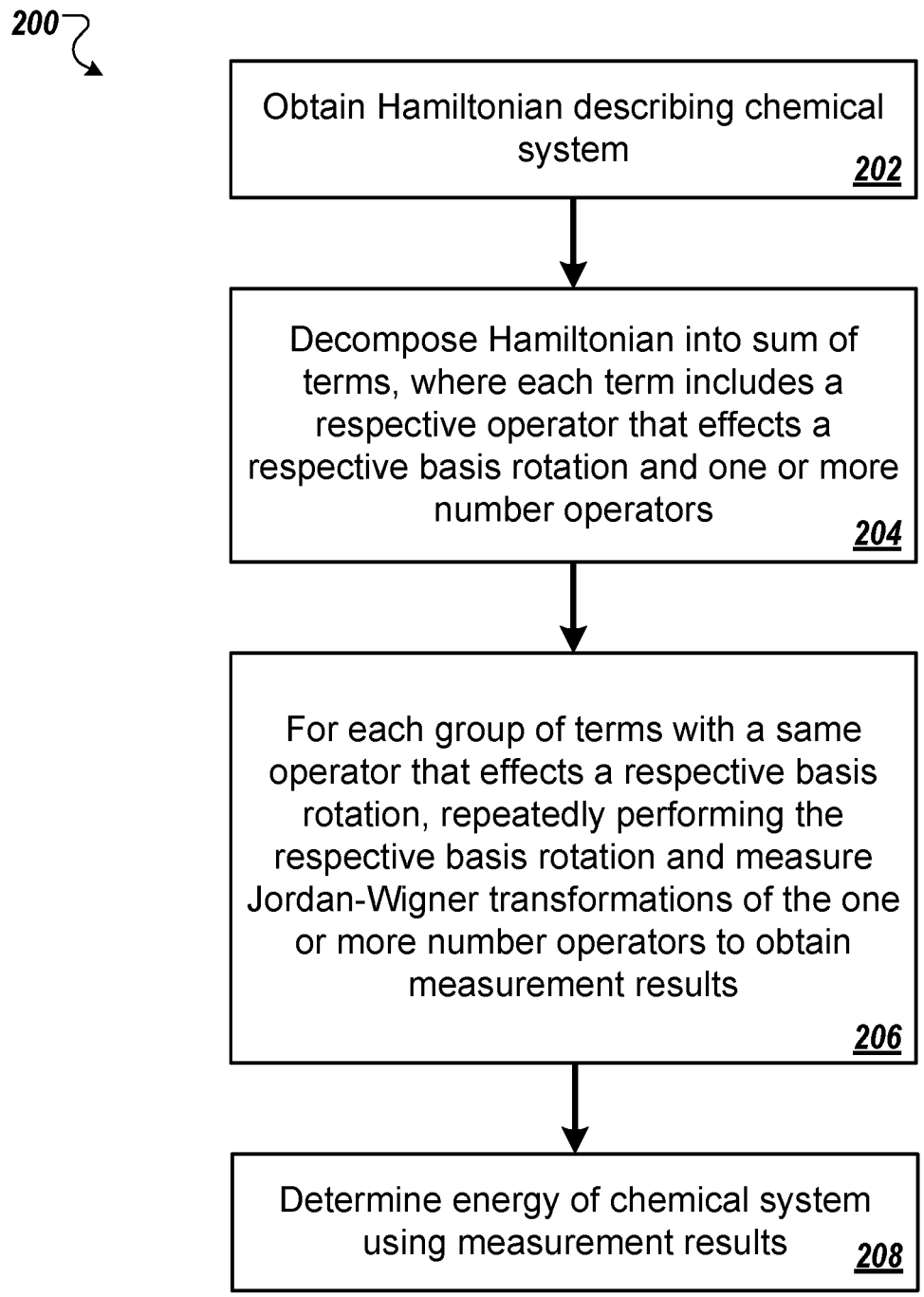
FIG. 2 is a flow diagram of an example process for measuring the energy of a chemical system.

FIG. 2 is a flow diagram of an example process 200 for measuring the energy of a quantum chemical system. For convenience, the process 200 will be described as being performed by a system of one or more classical or quantum computing devices located in one or more locations. For example, a quantum computation system, e.g., the system 100 of FIG. 1, appropriately programmed in accordance with this specification, can perform the process 200.

The system obtains a Hamiltonian describing the quantum chemical system (step 202). The Hamiltonian may be obtained by a classical computing device. The Hamiltonian may be input by a user, or may be retrieved from another source, e.g. a memory. The Hamiltonian describing the physical system may be expressed in an arbitrary orthonormal basis, e.g., a Gaussian or general molecular orbital basis. The Hamiltonian can include a one-electron and two-electron component, where each term in the one-electron component and two-electron component includes a respective scalar coefficient that may be given by known integrals over the basis functions dependent on the particular discretization scheme. An example Hamiltonian is given by Equation (1) below.

$$H = \sum_{pq} t_{pq} a_p^\dagger a_q + \sum_{pqrs} h_{pqrs} a_p^\dagger a_q a_r^\dagger a_s \qquad (1)$$

In Equation (1), $a_p$ and $a_p^\dagger$ represent annihilation and creation operators for spin orbital p, $t_{p,q}$, $h_{pqrs}$ represent the scalar coefficients that may be given by known integrals over the basis functions dependent on the particular discretization scheme. In some implementations the Hamiltonian may describe a periodic physical system. In other implementations the Hamiltonian may describe a non-periodic physical system, e.g., a single molecule.

The Hamiltonian describing the quantum chemical system can be mapped to a qubit Hilbert space using various approaches for simulating in-distinguishable fermions with distinguishable qubits. For example, the Hamiltonian describing the quantum chemical system can be mapped to a qubit Hilbert space using the Jordan-Wigner transformation or a Bravyi-Kitaev transformation.

The Jordan-Wigner transformation is appealing due to its simplicity and the fact that it allows for the explicit construction of a number of useful circuit primitives. However, one downside to using the Jordan-Wigner transformation is that the Jordan-Wigner transformation maps operators acting on a constant number of fermionic modes to qubit operators with support on up to N qubits. Under a simple model of readout error, e.g., a symmetric bit-flip channel, a Pauli word with support on L qubits has L opportunities for an error which reverses the sign of the measured value. This leads to the expectation value measurements which are driven to zero by a multiplicative factor which is exponentially small in L. As described below, a system implementing example process 200 can avoid this challenge without leaving the Jordan-Wigner framework, allowing estimation of one and two particle fermionic operator expectation values by the measurement of 1-local and 2-local qubit operators respectively.

The system performs a classical computation to decompose the Hamiltonian describing the chemical system into a sum of terms, wherein each term includes i) a respective operator that effects a respective single particle basis rotation, and ii) one or more particle density operators (also referred to as number operators) (step 204). That is, each term in the sum of terms corresponds to a respective single particle basis and each term in the sum is a diagonal operator. For example, the system can decompose the Hamiltonian given by Equation (1) above into Equation (2) below $$H = U_0\left(\sum_p c_p n_p\right)U_0^\dagger + \sum_{l=1}^{L}\omega_l U_l\left(\sum_{pq} c_{pq}^{(l)} n_p n_q\right)U_l^\dagger \quad (2)$$

where the operators $U_l$ represent the operators that effect respective single particle basis rotations, e.g., the single particle basis rotation given by Equation (3) below $$U_l \hat{a}_p^\dagger U_l^\dagger \to \sum_q k_{pq} \hat{a}_q \quad (3)$$

In some cases, Hamiltonians that describe chemical systems, e.g., Hamiltonians of the form given in Equation (1), can be difficult to simulate. For example, the Hamiltonian may describe a non-periodic system. Matrices representing Hamiltonians (expressed in a given basis) that describe periodic systems typically include an underlying structure that can be used to simplify calculations associated with simulating the periodic system, e.g., repetitions in the underlying structure can be used to reduce a number of multiplication operations needed to simulate the periodic system. However, matrices representing Hamiltonians (expressed in a given basis) that describe non-periodic systems may not include such underlying structures. Efficiently simulating such systems may therefore be challenging. However, by decomposing the Hamiltonian (expressed in an orthonormal basis) into the above described sum of terms, the Hamiltonian is mapped to a combination of sub Hamiltonians with a particular structure and expressed in different respective bases, where simulation techniques can be efficiently applied.

To decompose the Hamiltonian describing the chemical system into the sum of terms, the system first diagonalizes the scalar coefficients $h_{pqrs}$ of the terms in the two-electron component of the Hamiltonian by expressing each scalar coefficient as a respective sum of terms over the single particle bases. Each term in the sum of terms includes a product of a Hermitian coefficient matrix of one-body operators formed by a first pair of spin orbitals $g_{pq}^l$, a matrix $\omega_l$, and a Hermitian coefficient matrix of one-body operators formed by a second pair of spin orbitals $g_{rs}^l$. For example, the system can diagonalize the scalar coefficients $h_{pqrs}$ of the two-electron component of the Hamiltonian using Equation (4) below.

$$h_{pqrs} = \sum_{l=1}^{L} g_{pq}^l \omega_l g_{rs}^l \quad (4)$$

The two-electron component of the Hamiltonian can then be rewritten to obtain the Hamiltonian given in Equation (5) below.

$$\hat{H} = \sum_{pq,\alpha} t_{pq} \hat{a}_{p,\alpha}^\dagger \hat{a}_{q,\alpha} + \sum_{l=1}^{L} \omega_l \left(\sum_{pq,\alpha} g_{pq}^l \hat{a}_{p,\alpha}^\dagger \hat{a}_{q,\alpha}\right)^2 \quad (5)$$

where $t_{pq}$ and each of the $g_{pq}^l$ (for fixed l) are Hermitian coefficient matrices of one-body operators.

The system then determines matrices $\hat{u}_l$ that diagonalize respective Hermitian coefficient matrices of one-body operators in their respective single particle Hilbert spaces. The system determines the operators $\hat{U}_l^\vee$ that effect respective single particle basis rotations required to obtain Equation (2) using the determined matrices $\hat{u}_l$.

In some implementations the system can discard finite eigenvalues that are smaller than a predetermined threshold during the processing for decomposing the Hamiltonian describing the chemical system into the sum of terms, e.g., to obtain a controllable approximation to the original Hamiltonian. The predetermined threshold may be selected in advance based on the particular quantum chemical system (or, equivalently, the Hamiltonian describing the quantum chemical system) and/or the capabilities of the hardware used to perform step 206. For example, to yield a more controllable approximation a larger threshold may be used, i.e., more eigenvalues may be discarded.

The system groups (step 206) terms of the decomposed Hamiltonian that are diagonal in the same single particle basis l. For example, for each term in the decomposed Hamiltonian given by Equation (2) above the system can determine in which single particle basis the term diagonalizes and assign the term to a group corresponding to the single particle basis.

The system then measures (step 206), for each group, expectation values of the terms included in the group. Within a group, the measurement of the terms can be performed approximately simultaneously, e.g., within the limits of hardware precision.

To measure the expectation values of the terms included in a group, the system performs, by quantum computation, the basis rotation corresponding to the group on a qubit system encoding a state of the chemical system that is to be measured. For example, the system can apply a respective Givens rotation circuit to the qubit system. The system then measures the qubit system. This includes measuring, in the computational basis, Jordan-Wigner transformations of the one or more particle density operators included in the terms to obtain a respective measurement result. That is, by performing the basis rotation, e.g., applying a corresponding $U_l$ circuit, directly on a quantum state of the qubit system prior to measurement, the system can then simultaneously sample the $\langle n_p \rangle$ and $\langle n_p n_q \rangle$ expectation values in the rotated basis to estimate the energy as $\langle H \rangle = \sum_p c_p \langle n_p \rangle_0 + \sum_{l=1}^{L}(\sum_{pq} c_{pq}^{(l)} \langle n_p n_q \rangle_l)$ where the subscript l on the expectation values represents that they are sampled after applying the basis transformation $U_l$.

The reason that $\langle n_p \rangle$ and $\langle n_p n_q \rangle$ can be sampled simultaneously is because under the Jordan-Wigner transformation, $n_p = (\mathbb{I} + \mathbb{Z}_p)/2$, which is a diagonal qubit operator. Therefore, the system is able to sample all terms in the Hamiltonian with only $L+1$ distinct term groups. Fortunately, the $U_l$ are extremely easy to implement, even on hardware with minimal connectivity. For example, any change of single-particle basis can be performed using $(N^2-N)/8$ two qubit gates and gate depth of exactly N even with only a linearly connected array of qubits.

The system can repeatedly, e.g., a predetermined number of times, measure the expectation values of the terms included in a group to obtain multiple measurement results, and post process the multiple measurement results to obtain a final measurement result. For example, the system may post select measurement results from the multiple measurement results and/or determine a statistical average over the multiple measurement results. An example process for performing error mitigation using post selection is described below with reference to FIG. 4.

The system determines, by classical computation, the energy of the chemical system using the obtained measurement results for each of the groups (step 208), for example by adding determined averages of measurement results corresponding to each group. In some implementations the system can perform further computations using the determined energy of the chemical system to determine properties of the physical system. For example, example process 200 can be used to determine properties of single molecules and simulate catalysts or pharmaceuticals, for performing material science simulations, or for determining the rates of chemical reactions.

Figure 3A:
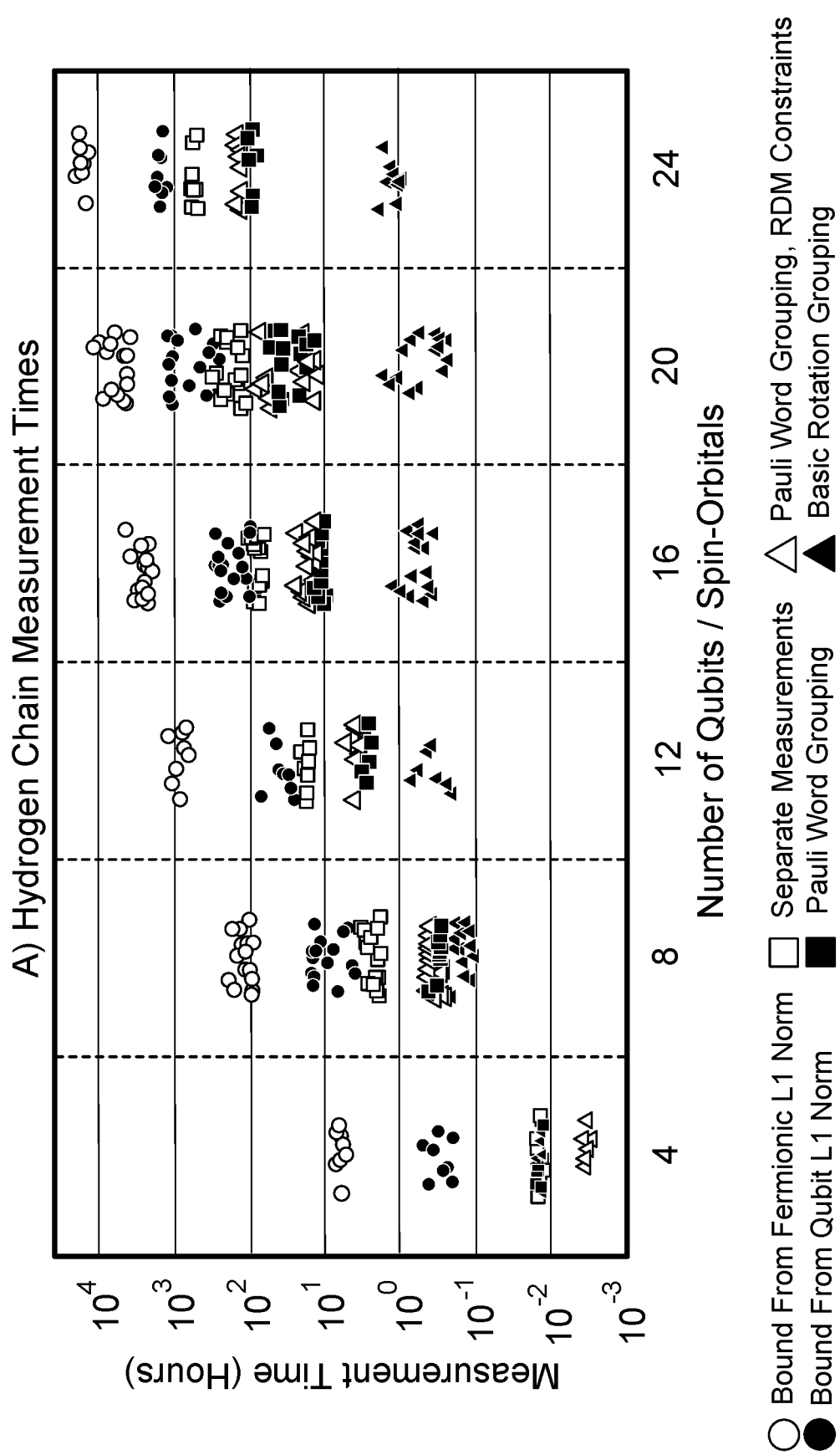
FIGS. 3A-3C show example measurement times plotted against number of qubits/spin orbitals for different measurement strategies and different chemical systems.
Figure 3B:
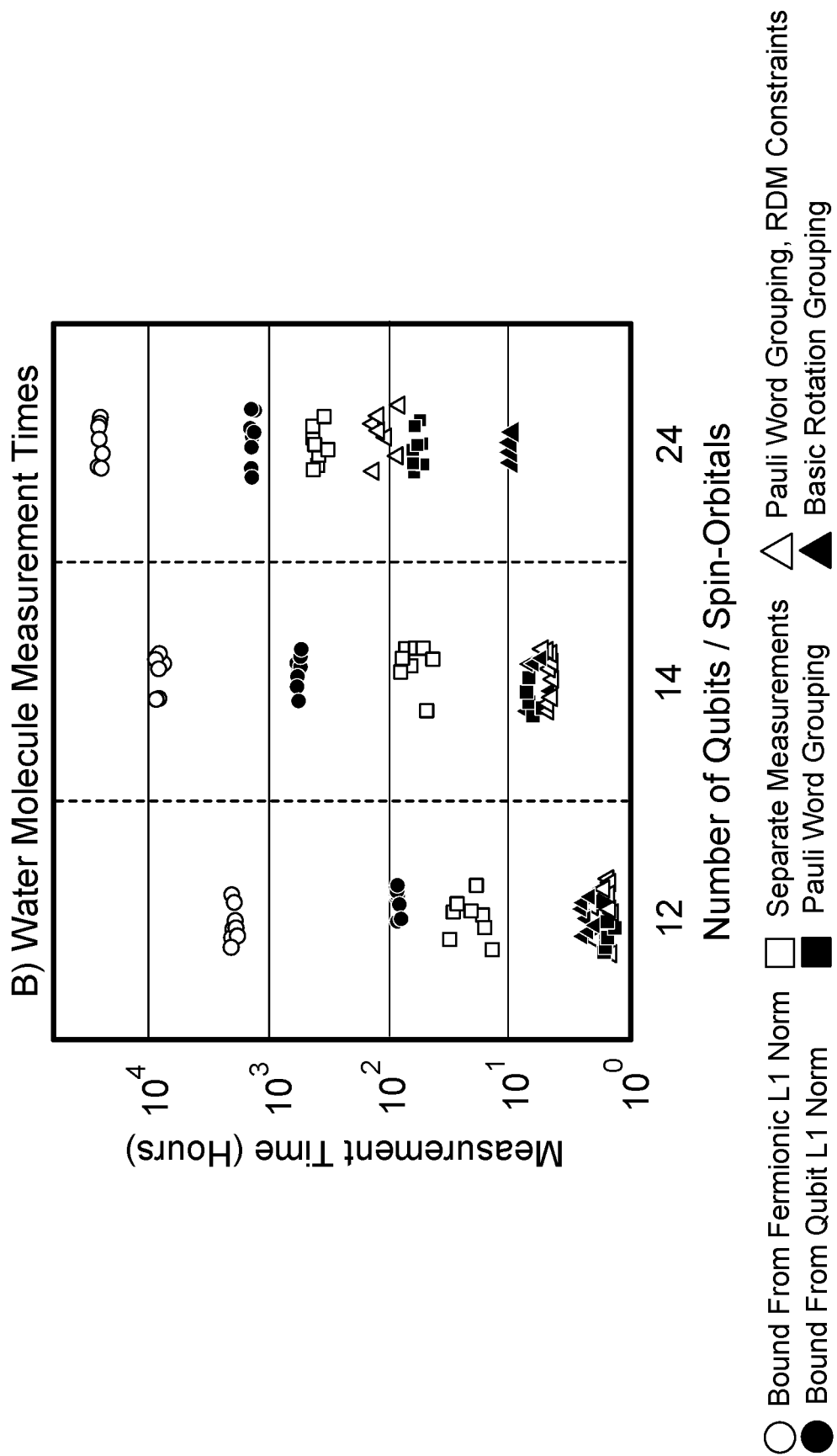
Figure 3C:
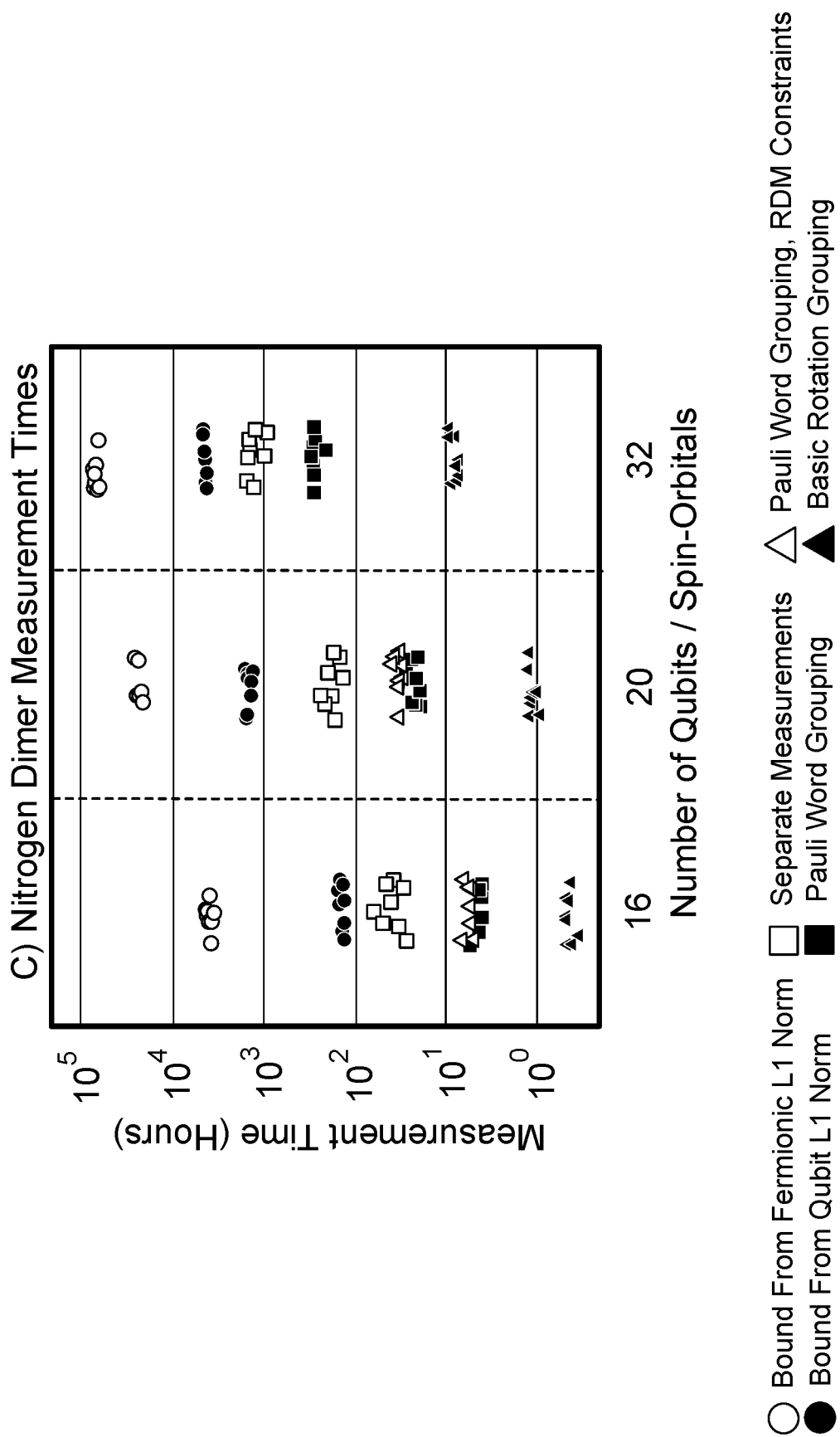

FIGS. 3A-3C show example measurement times (times required to obtain an estimate of the ground state energy) plotted against number of qubits/spin orbitals for different chemical systems and different measurement strategies/methods, namely the presently described measurement strategy (referred to as "Basis rotation grouping"), three existing measurement strategies ("Separate measurements," "Pauli word grouping," and "Pauli word grouping, RDM constraints") and two upper bounds from the Fermionic L1 norm and qubit L1 norm.

The data plotted in FIGS. 3A-3C is generated using calculations of the variance of expectation values to determine the measurement time required assuming 10,000 circuit repetitions per second with measurements distributed optimally, e.g., according to known prescriptions such as those that demand that each operator $\hat{O}_i$ is measured as a fraction of the time $f_i$ via $f_i = \sqrt{\text{Var}(\hat{O}_i)}/\Sigma_j \sqrt{\text{Var}(\hat{O}_j)}$. Since in practice the variance of each operator is not known ahead of time, it is assumed that an adaptive measurement scheme which schedules additional measurements based on the observed sample variance can approximate the ideal partitioning of measurement time and for simplicity FIGS. 3A-3C only present numbers based on the ideal partitioning. A target precision corresponding to a 2σ error bar of 1.0 millihartree is assumed.

The calculations performed to generate the data plotted in FIG. 3 are performed for symmetrically stretched Hydrogen chains with various bond lengths and numbers of atoms (FIG. 3A), a symmetrically stretched water molecule (FIG. 3B), and a stretched Nitrogen dimer (FIG. 3C), all in multiple basis sets. All calculations on systems up to 20 qubits use the configuration interaction singles and doubles (CISD) approximation to the ground state, and those with more than 20 qubits are performed with the Hartree-Fock state. The bounds based on the L1 norm are calculated both in the fermionic Hilbert space and in terms of the operators acting directly on qubits.

FIG. 3A shows data generated for symmetrically stretched Hydrogen chains with various bond lengths and numbers of atoms, in multiple basis sets. The Hydrogen chains contain between 2 and 10 atoms at a symmetric interatomic spacing between 0.6 and 1.3 Å in STO-3G, 6-31G, or cc-pVDZ basis sets. Calculations performed on systems which require the same number of qubits (spin-orbitals) are plotted together in columns and spread slightly horizontally for visibility.

FIG. 3B shows data generated for a symmetrically stretched water molecule in multiple basis sets. The bonds in the water molecule are symmetrically stretched between 0.8 and 1.5 Å. The water calculations are performed in STO-3G basis sets with and without the 1 s orbitals on the Nitrogen/Oxygen molecules frozen and in the 6-31G basis set with a frozen core. Calculations performed on systems which require the same number of qubits (spin-orbitals) are plotted together in columns and spread slightly horizontally for visibility.

FIG. 3C shows data generated for a stretched Nitrogen dimer in multiple basis sets. The spacing between the Nitrogen atoms ranges from 0.9 to 1.6 Å. The Nitrogen calculations are performed in STO-3G basis sets with and without the is orbitals on the Nitrogen/Oxygen molecules frozen and in the 6-31G basis set with a frozen core. Calculations performed on systems which require the same number of qubits (spin-orbitals) are plotted together in columns and spread slightly horizontally for visibility.

Each of FIGS. 3A-3C demonstrate the effectiveness of the presently described measurement strategy in comparison to each of the three existing measurement strategies and the two L1 norm values. For example, for a system size larger or equal to 12 qubits in the case of a hydrogen chain, 24 qubits for water molecules, and 16 qubits for a nitrogen dimer the measurement time is reduced using the presently described method of basis rotation grouping. Further, for an increasing number of qubits, that is increasing system size, the relative improvement in measurement time between the presently described method and the other existing methods increases.

Beyond the reduction in measurement time, the measurement strategy described above with reference to example process 200 has the additional benefits of reducing susceptibility to readout errors and enabling a powerful form of error mitigation by post-selection. These properties are a result of the fact that the Hamiltonian that is measured in example process 200 is measured only in terms of particle density operators in different basis sets. As described above, applying the Jordan-Wigner transformation to the terms of the quantum chemical Hamiltonian leads to operators with support on up to N qubits. Particle density operators however transform more simply $\hat{n}_i \rightarrow (\hat{Z}_i + \hat{\mathbb{I}})/2$. Therefore, the measurement strategy described in example process 200 avoids the expansion of locality caused by long Jordan-Wigner strings and individual terms from the one and two-particle components of the Hamiltonian can be measured by measuring 1-local and 2-local qubit operators respectively.

In addition, the presently described measurement strategy provides an opportunity for mitigating errors. For example, when states with a definite eigenvalue of a symmetry operator, such as the total particle number, $\hat{N}$, or the z-component of spin, $\hat{S}_z$, are of interest, it is advantageous to have a method that removes the components of some experimentally prepared state p which violate that constraint.

Two strategies to accomplish this exist. A first existing strategy includes directly and non-destructively measuring the symmetry operator and discarding those outcomes where the undesired eigenvalue is observed, projecting into the proper symmetry sector by post-selection. The difficulty in performing these measurements efficiently has restricted the application of this strategy. In addition, some implementations of this first existing strategy focus on measuring the parities of $\hat{N}$ and $\hat{S}_z$ using circuits with O(N) depth, which may induce further errors during their implementation. A second existing strategy builds on the first and uses additional measurements and classical post-processing to calculate expectation values of the projected state without requiring additional circuit depth.

The presently described measurement strategy enables a new form of error mitigation that is based on post selection and eliminates the challenges posed by the non-locality of Jordan-Wigner transformed operators during measurement, as described below with reference to FIG. 4.

Error Mitigation by Post Selection

Figure 4:
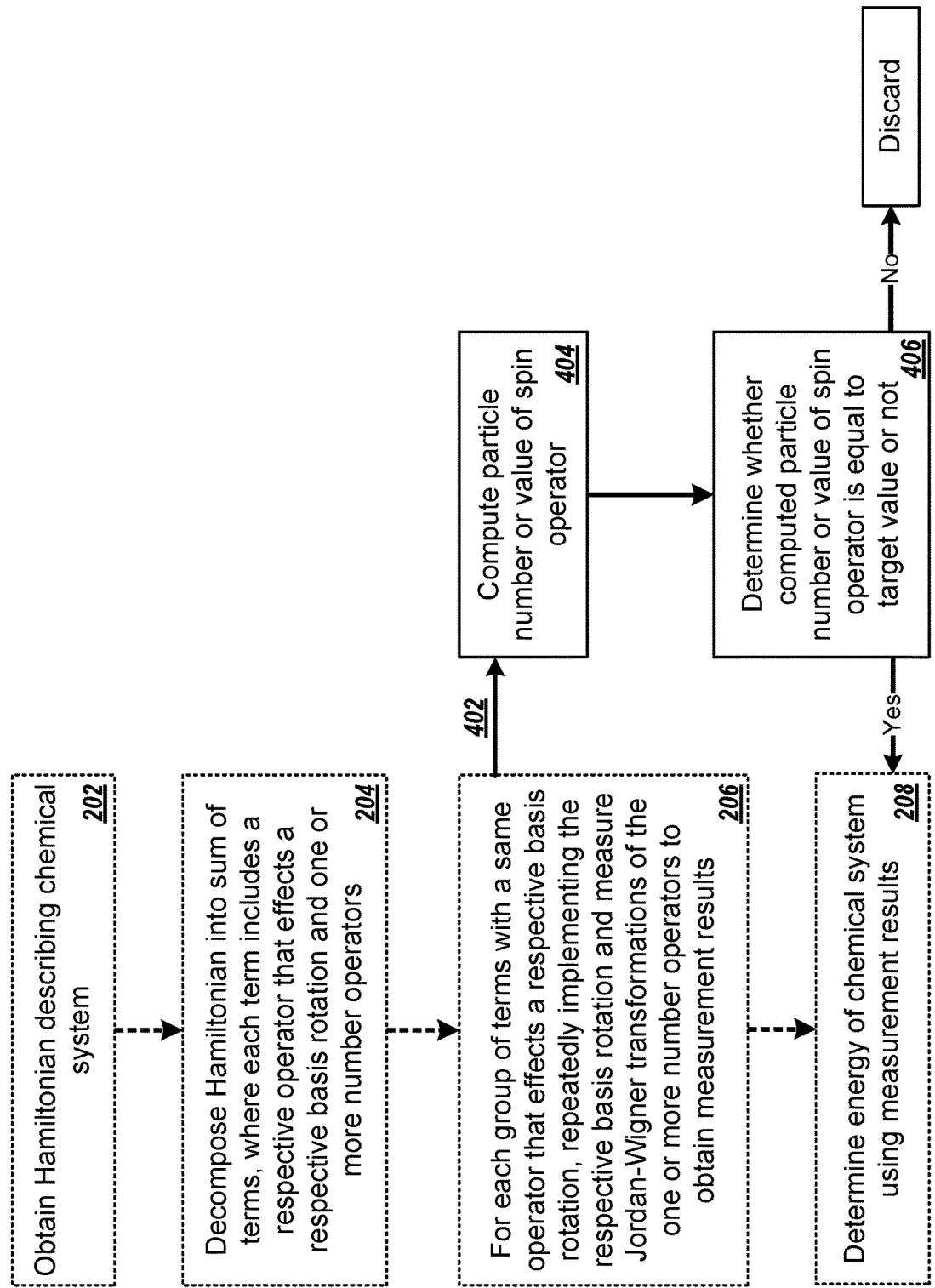
FIG. 4 is a flow diagram of an example process for performing error mitigation using post selection.

FIG. 4. is a flow diagram of an example process 400 for performing error mitigation using post selection. Example process 400 can be performed in conjunction with example process 200 for measuring the energy of a chemical system, as described above.

For convenience, the process 400 will be described as being performed by a system of one or more classical or quantum computing devices located in one or more locations. For example, a quantum computation system, e.g., the system 100 of FIG. 1, appropriately programmed in accordance with this specification, can perform the process 400.

The system obtains a measurement result produced during step 206 of example process 200 (step 402). That is, the system obtains a measurement result representing an outcome of measuring a group of terms with a same operator that effects a respective basis rotation by implementing the respective basis rotation by applying a respective Givens rotation circuit to a qubit system and measuring Jordan-Wigner transformations of the one or more number operators included in the terms in the computational basis.

The system computes a total particle number or value of a spin component, e.g., the z component of spin, using the obtained measurement result (step 404). Since the obtained measurement results consist of bit strings the system can compute a total particle number by counting 1s or 0s, or compute the value of a spin component by summing the particle density operators acting on "up spin" spin-orbitals minus the sum of the particle density operators acting on the "down spin" spin-orbitals (and dividing by two).

The system determines whether the computed total particle number or value of a spin component is equal to a respective target value. In response to determining that the computed total particle number or spin number is equal to a respective target value, the system determines that no error has occurred and provides the measurement result for post processing, as described above with reference to FIG. 2. In response to determining that the computed total particle number or spin number is not equal to a respective target value, the system determines that an error has occurred and discards the measurement result.

Figure 5:
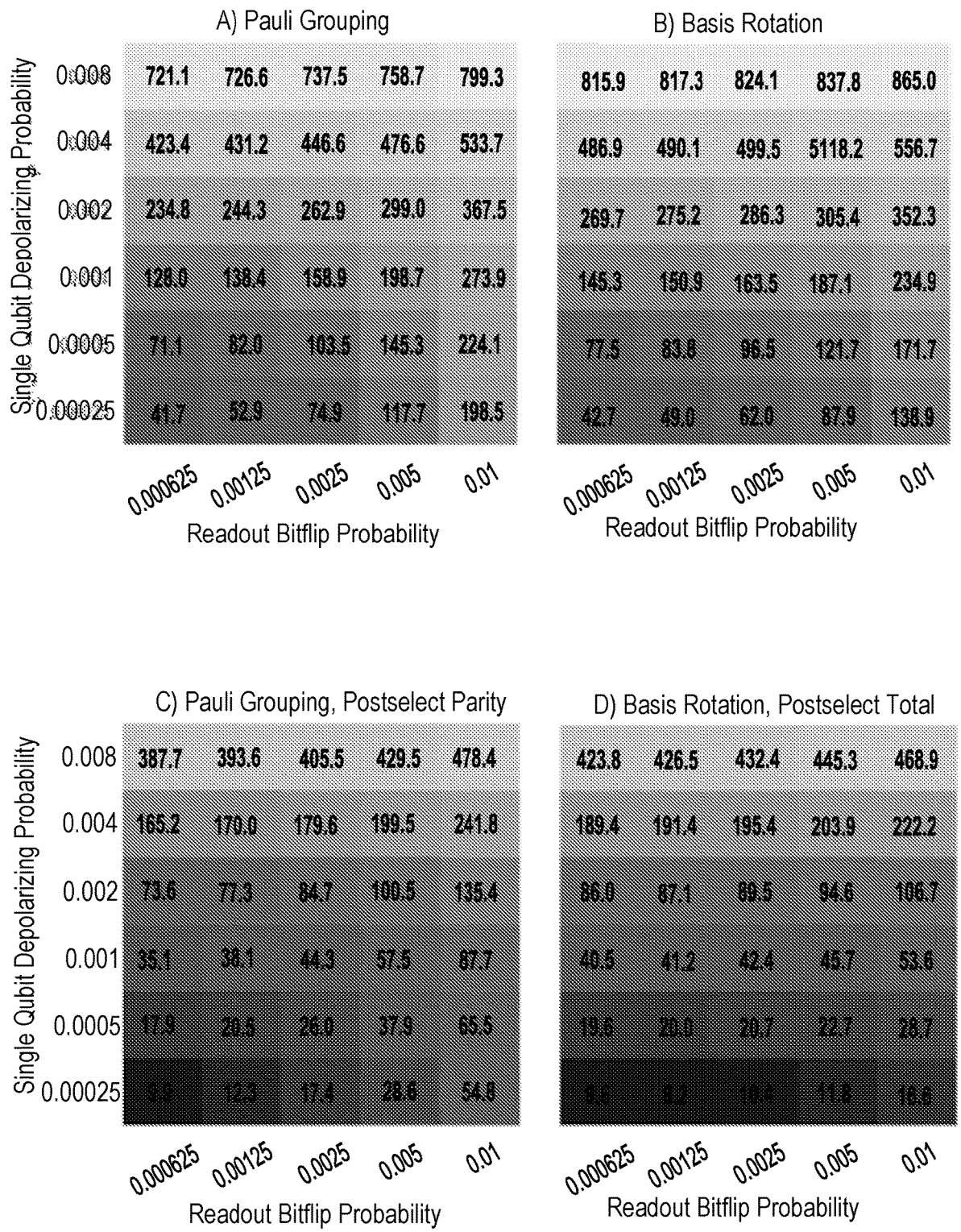
FIG. 5 shows single qubit depolarizing probability plotted against readout bit flip probability for ground state measurements of a stretched chain of six qubits Hydrogen atoms.

FIG. 5 shows single qubit depolarizing probability plotted against readout bit flip probability for ground state measurements of a stretched chain of six Hydrogen atoms under an error model composed of single qubit dephasing noise applied after every two qubit gate together with a symmetric bit flip channel during readout. FIG. 5 shows four plots A-D that correspond to different measurement strategies. In each plot, squares and numbers represent absolute errors in millihartrees.

Plot A shows the error incurred by a "Pauli Grouping" measurement strategy involving simultaneously measuring compatible Pauli words in the usual molecular orbital basis. Plot B shows the error when using the presently described "Basis Rotation" or "Basis Rotation Grouping" scheme which performs a change of single-particle basis before measurement. Plot C shows the errors using the "Pauli grouping strategy" together with additional measurements and post-processing which effectively project the measured state onto a manifold with the correct parities of the total particle number and $\hat{S}_z$ operators. Plot D shows the errors found when using the presently described basis rotation strategy and post selecting on outcomes where the correct particle number and $\hat{S}_z$ were observed. For the purposes of approximating a realistic ansatz circuit, three random Givens rotation networks which compose to the identity were simulated acting on the ground state prior to measurement.

FIG. 5 shows that the amount of errors incurred using the presently described measurement strategy (with and without post selection techniques) can be smaller than the amount of errors incurred using a Pauli grouping measurement strategy (with and without post selection techniques). In addition, both the Pauli grouping strategy and the basis rotation strategy benefit from implementing post selection error mitigation techniques. In addition, despite the fact that the presently claimed basis rotation strategy requires circuits that are a third again as deep as those used for the Paul grouping strategy, the errors remaining after post selection error mitigation are comparable in many regimes and lower when noise during measurement is the dominant error channel. Even without post selection, where the presently described measurement strategy benefits from a strictly more powerful form of error mitigation, the locality of the presently described Jordan-Wigner transformed operators provides some benefit in suppressing the impact of readout errors.

Implementations of the digital and/or quantum subject matter and the digital functional operations and quantum operations described in this specification can be implemented in digital electronic circuitry, suitable quantum circuitry or, more generally, quantum computational systems, in tangibly-embodied digital and/or quantum computer software or firmware, in digital and/or quantum computer hardware, including the structures disclosed in this specification and their structural equivalents, or in combinations of one or more of them. The term "quantum computational systems" may include, but is not limited to, quantum computers, quantum information processing systems, quantum cryptography systems, or quantum simulators.

Implementations of the digital and/or quantum subject matter described in this specification can be implemented as one or more digital and/or quantum computer programs, i.e., one or more modules of digital and/or quantum computer program instructions encoded on a tangible non-transitory storage medium for execution by, or to control the operation of, data processing apparatus. The digital and/or quantum computer storage medium can be a machine-readable storage device, a machine-readable storage substrate, a random or serial access memory device, one or more qubits, or a combination of one or more of them. Alternatively or in addition, the program instructions can be encoded on an artificially-generated propagated signal that is capable of encoding digital and/or quantum information, e.g., a machine-generated electrical, optical, or electromagnetic signal, that is generated to encode digital and/or quantum information for transmission to suitable receiver apparatus for execution by a data processing apparatus.

The terms quantum information and quantum data refer to information or data that is carried by, held or stored in quantum systems, where the smallest non-trivial system is a qubit, i.e., a system that defines the unit of quantum information. It is understood that the term "qubit" encompasses all quantum systems that may be suitably approximated as a two-level system in the corresponding context. Such quantum systems may include multi-level systems, e.g., with two or more levels. By way of example, such systems can include atoms, electrons, photons, ions or superconducting qubits. In many implementations the computational basis states are identified with the ground and first excited states, however it is understood that other setups where the computational states are identified with higher level excited states are possible.

The term "data processing apparatus" refers to digital and/or quantum data processing hardware and encompasses all kinds of apparatus, devices, and machines for processing digital and/or quantum data, including by way of example a programmable digital processor, a programmable quantum processor, a digital computer, a quantum computer, multiple digital and quantum processors or computers, and combinations thereof. The apparatus can also be, or further include, special purpose logic circuitry, e.g., an FPGA (field programmable gate array), an ASIC (application-specific integrated circuit), or a quantum simulator, i.e., a quantum data processing apparatus that is designed to simulate or produce information about a specific quantum system. In particular, a quantum simulator is a special purpose quantum computer that does not have the capability to perform universal quantum computation. The apparatus can optionally include, in addition to hardware, code that creates an execution environment for digital and/or quantum computer programs, e.g., code that constitutes processor firmware, a protocol stack, a database management system, an operating system, or a combination of one or more of them.

A digital computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a digital computing environment. A quantum computer program, which may also be referred to or described as a program, software, a software application, a module, a software module, a script, or code, can be written in any form of programming language, including compiled or interpreted languages, or declarative or procedural languages, and translated into a suitable quantum programming language, or can be written in a quantum programming language, e.g., QCL or Quipper.

A digital and/or quantum computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A digital and/or quantum computer program can be deployed to be executed on one digital or one quantum computer or on multiple digital and/or quantum computers that are located at one site or distributed across multiple sites and interconnected by a digital and/or quantum data communication network. A quantum data communication network is understood to be a network that may transmit quantum data using quantum systems, e.g. qubits. Generally, a digital data communication network cannot transmit quantum data, however a quantum data communication network may transmit both quantum data and digital data.

The processes and logic flows described in this specification can be performed by one or more programmable digital and/or quantum computers, operating with one or more digital and/or quantum processors, as appropriate, executing one or more digital and/or quantum computer programs to perform functions by operating on input digital and quantum data and generating output. The processes and logic flows can also be performed by, and apparatus can also be implemented as, special purpose logic circuitry, e.g., an FPGA or an ASIC, or a quantum simulator, or by a combination of special purpose logic circuitry or quantum simulators and one or more programmed digital and/or quantum computers.

For a system of one or more digital and/or quantum computers to be "configured to" perform particular operations or actions means that the system has installed on it software, firmware, hardware, or a combination of them that in operation cause the system to perform the operations or actions. For one or more digital and/or quantum computer programs to be configured to perform particular operations or actions means that the one or more programs include instructions that, when executed by digital and/or quantum data processing apparatus, cause the apparatus to perform the operations or actions. A quantum computer may receive instructions from a digital computer that, when executed by the quantum computing apparatus, cause the apparatus to perform the operations or actions.

Digital and/or quantum computers suitable for the execution of a digital and/or quantum computer program can be based on general or special purpose digital and/or quantum processors or both, or any other kind of central digital and/or quantum processing unit. Generally, a central digital and/or quantum processing unit will receive instructions and digital and/or quantum data from a read-only memory, a random access memory, or quantum systems suitable for transmitting quantum data, e.g. photons, or combinations thereof.

The essential elements of a digital and/or quantum computer are a central processing unit for performing or executing instructions and one or more memory devices for storing instructions and digital and/or quantum data. The central processing unit and the memory can be supplemented by, or incorporated in, special purpose logic circuitry or quantum simulators. Generally, a digital and/or quantum computer will also include, or be operatively coupled to receive digital and/or quantum data from or transfer digital and/or quantum data to, or both, one or more mass storage devices for storing digital and/or quantum data, e.g., magnetic, magneto-optical disks, optical disks, or quantum systems suitable for storing quantum information. However, a digital and/or quantum computer need not have such devices.

Digital and/or quantum computer-readable media suitable for storing digital and/or quantum computer program instructions and digital and/or quantum data include all forms of non-volatile digital and/or quantum memory, media and memory devices, including by way of example semiconductor memory devices, e.g., EPROM, EEPROM, and flash memory devices; magnetic disks, e.g., internal hard disks or removable disks; magneto-optical disks; CD-ROM and DVD-ROM disks; and quantum systems, e.g., trapped atoms or electrons. It is understood that quantum memories are devices that can store quantum data for a long time with high fidelity and efficiency, e.g., light-matter interfaces where light is used for transmission and matter for storing and preserving the quantum features of quantum data such as superposition or quantum coherence.

Control of the various systems described in this specification, or portions of them, can be implemented in a digital and/or quantum computer program product that includes instructions that are stored on one or more non-transitory machine-readable storage media, and that are executable on one or more digital and/or quantum processing devices. The systems described in this specification, or portions of them, can each be implemented as an apparatus, method, or system that may include one or more digital and/or quantum processing devices and memory to store executable instructions to perform the operations described in this specification.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by a classical processor and quantum computing hardware in data communication with the classical processor, the method comprising:
   measuring an energy of a chemical system, comprising:
      obtaining, as input to the classical processor, a Hamiltonian describing the chemical system, wherein the Hamiltonian is expressed in an orthonormal basis;
      implementing, by the classical processor and the quantum computing hardware, a basis rotation grouping measurement strategy of a qubit system included in the quantum computing hardware, the basis rotation grouping measurement strategy comprising:
         decomposing, by classical computation, the Hamiltonian describing the chemical system into a sum of terms, wherein each term comprises i) a respective operator that effects a respective single particle basis rotation, and ii) one or more particle density operators;
         for each group comprising terms with a same operator that effects a respective single particle basis rotation, measuring expectation values of the terms included in the group, comprising, for each repetition in a plurality of repetitions, wherein a number of repetitions in the plurality of repetitions is dependent on a predetermined accuracy:
            encoding, by quantum computation on the quantum computing hardware, a state of the chemical system in a state of the qubit system;
            performing, by quantum computation on the quantum computing hardware, the respective single particle basis rotation of the group on the state of the qubit system encoding the state of the chemical system, comprising applying a quantum circuit to the qubit system; and
            measuring, by quantum computation on the quantum computing hardware and in a computational basis, the qubit system, comprising measuring Jordan-Wigner transformations of the one or more particle density operators in the group to obtain a respective measurement result for the group; and
         determining, by classical computation, the energy of the chemical system using the obtained measurement results.

2. The method of claim 1, wherein measuring expectation values of the terms included in the group further comprises performing error mitigation by post selection.

3. The method of claim 2, wherein performing error mitigation by post selection comprises:
   computing a total particle number or spin component using the obtained measurement result;
   determining whether the computed total particle number or spin component is equal to a respective target value;
   in response to determining that the computed total particle number or spin component is equal to a respective target value, providing the measurement result for determining, by classical computation, the energy of the chemical system; and
   in response to determining that the computed total particle number or spin component is not equal to a respective target value, discarding the measurement result.

4. The method of claim 1, wherein the Hamiltonian describing the chemical system comprises a one-electron component and a two-electron component, and wherein decomposing, by classical computation, the Hamiltonian describing the chemical system into a sum of terms comprises:
   diagonalizing each scalar coefficient in the two-electron component, comprising representing each scalar coefficient in the two-electron component as a second sum of terms over the single particle bases, each term in the second sum of terms comprising a product of a Hermitian coefficient matrix of one-body operators formed by a first pair of spin orbitals, a matrix, and a Hermitian coefficient matrix of one-body operators formed by a second pair of spin orbitals;

determining, for each term in the sum of terms, a matrix that diagonalizes the one-body operators in the respective Hermitian coefficient matrices; and determining the respective operators that effect the respective basis rotations using the determined matrices that diagonalize the one-body operators.

5. The method of claim 4, further comprising discarding finite eigenvalues smaller than a predetermined threshold.

6. The method of claim 1, further comprising grouping terms of the decomposed Hamiltonian that are diagonal in the same single particle basis, comprising, for each term in the decomposed Hamiltonian:

determining which single particle basis the term diagonalizes; and assigning the term to a group corresponding to the determined single particle basis.

7. The method of claim 1, wherein measuring expectation values of the terms included in the group comprises measuring the expectation values of the terms included in the group simultaneously.

8. The method of claim 1, wherein performing the respective basis rotation comprises applying a respective Givens rotation circuit to the qubit system.

9. The method of claim 1, wherein determining, by classical computation, the energy of the chemical system using the obtained measurement results comprises:

determining an average measurement result corresponding to each group; and adding the determined averages.

10. The method of claim 1, wherein the arbitrary orthonormal basis comprises a Gaussian or molecular orbital basis.

11. The method of claim 1, wherein the Hamiltonian describing the chemical system comprises multiple terms each comprising products of one or more of i) annihilation operators for respective spin orbitals, ii) creation operators for respective spin orbitals, and ii) scalar coefficients given by one- or two-electron integrals over basis functions in the orthonormal basis.

12. The method of claim 1, wherein the chemical system comprises a symmetrically stretched Hydrogen chain, symmetrically stretched water molecule, or a stretched Nitrogen dimer.

13. An apparatus comprising:
quantum computing hardware; and
one or more classical processors;
wherein the apparatus is configured to perform operations comprising:

obtaining, as input to the one or more classical processors, a Hamiltonian describing a chemical system, wherein the Hamiltonian is expressed in an orthonormal basis;

implementing, by the one or more classical processors and the quantum computing hardware, a basis rotation grouping measurement strategy of a qubit system included in the quantum computing hardware, the basis rotation grouping measurement strategy comprising:

decomposing, by classical computation, the Hamiltonian describing the chemical system into a sum of terms, wherein each term comprises i) a respective operator that effects a respective single particle basis rotation, and ii) one or more particle density operators;

for each group comprising terms with a same operator that effects a respective single particle basis rotation, measuring expectation values of the terms included in the group, comprising, for each repetition in a plurality of repetitions, wherein a number of repetitions in the plurality of repetitions is dependent on a predetermined accuracy:

encoding, by quantum computation on the quantum computing hardware, a state of the chemical system in a state of the qubit system;

performing, by quantum computation on the quantum computing hardware, the respective single particle basis rotation on the state of the qubit system encoding the state of the chemical system, comprising applying a quantum circuit to the qubit system; and measuring, by quantum computation on the quantum computing hardware and in a computational basis, the qubit system, comprising measuring Jordan-Wigner transformations of the one or more particle density operators in the group to obtain a respective measurement result for the group; and determining, by classical computation, the energy of the chemical system using the obtained measurement results.

* * * * *